United States Patent [19]
Courtney et al.

[11] Patent Number: 5,139,339
[45] Date of Patent: Aug. 18, 1992

[54] MEDIA DISCRIMINATING AND MEDIA PRESENCE SENSOR

[75] Inventors: John E. Courtney, Macedon; Fred F. Hubble, III., Rochester, both of N.Y.; Kenneth I. Chan, Milpitas, Calif.

[73] Assignee: Xerox Corporation, Stamford, Conn.

[21] Appl. No.: 457,067

[22] Filed: Dec. 26, 1989

[51] Int. Cl.⁵ .............................................. G01N 21/47
[52] U.S. Cl. ..................................... 356/446; 250/341; 250/561; 355/311
[58] Field of Search .................... 356/446, 73, 445; 250/561, 223 R, 341; 271/245, 265; 355/203, 311, 221, 296, 313, 310

[56] References Cited
U.S. PATENT DOCUMENTS

| | | | |
|---|---|---|---|
| 3,435,240 | 3/1969 | Brunton | 250/219 |
| 4,092,068 | 5/1978 | Lucas et al. | 356/73 |
| 4,525,630 | 6/1985 | Chapman | 250/572 |
| 4,540,887 | 9/1985 | Minerd | 250/561 |
| 4,754,148 | 6/1988 | Barkowski | 250/571 |
| 4,967,094 | 10/1990 | Horton et al. | 250/561 |

Primary Examiner—Vincent P. McGraw
Assistant Examiner—LaCharles P. Keesee, II
Attorney, Agent, or Firm—William A. Henry

[57] ABSTRACT

A media discriminating and presence sensor that can detect and discriminate between paper and transparency uses a light emitting diode and two defectors configured so as to measure both diffuse and specular reflectivity of the media, and a media support surface that suppresses unwanted reflections.

11 Claims, 3 Drawing Sheets

MEDIA DISCRIMINATING AND MEDIA PRESENCE SENSOR

This invention relates to media sensors, and in particular, to sensors that can discriminate between paper and a transparency traveling within a paper path.

In the xerographic printing process there is a problem when using different media such as transparency and paper because they each require different fusing time and/or temperature to obtain excellent copies. Therefore, it would be desirable to know what the media is so that the machine can be set to compensate for each different media and thereby ensure excellent copies.

Typical prior art sensors are shown in U.S. Pat. Nos. 3,435,240 and 4,092,068. In U.S. Pat. No. 3,435,240, the surface characteristics of a material are determined by the quotient of output signals from two photomultipliers. The magnitude of these signals from the photomultipliers is determined by the simultaneous transmittance of energy from a single light source through small and large areas of a material being examined. In U.S. Pat. No. 4,092,068, a single light source is directed onto a material surface and the surface characteristics are examined by comparing the amount of light reflected at two different angles from the surface onto a pair of detectors.

It is also known in the prior art to provide sensors to be able to detect translucent papers. One technique comprises a light emitter on one side of the paper path and a transmittance detector on the other side of the path. As paper enters the path between the emitter and detector, the light may be attenuated sufficiently through the paper in order that the signal sensed by the detector indicates paper in the path. The difficulty is that the signal sensed by the detector indicates paper in the path. The difficulty is that the sensor circuitry is generally tuned only to detect paper having a particular transmittance characteristic. For papers or documents having different transmittance characteristics, the sensor circuitry is often too insensitive to be able to detect this type of paper without adjustments having to be made to the sensor circuitry.

Another technique of paper sensing is to provide a reflectance detector on the same side of the paper as the light emitter. With paper in the path, a predetermined amount of light will be reflected from the paper to the reflectance detector to indicate the presence of paper. Here again, the sensing circuitry is often sensitive only to a document or paper having certain transmittance characteristics and for papers with different characteristics, it is necessary to adjust the detector circuitry. This is due to the fact that the present sensor systems have a wide range of characteristics and, therefore, very low effective contrast ratios. Because of the low contrast ratios obtained in a manufacturing or field environment, electrical and/or mechanical adjustments are required for different documents. The need for readjustment for different types of papers often renders the sensors impractical for use in applications having a wide variety of papers.

A paper detector is shown in U.S. Pat. No. 4,540,887 that is optimized for attenuation of a signal reflected from paper. Light is reflected from the paper and is picked up by a detector. However, this signal must be a fraction of the light picked up from a mirror when no paper is present, i.e., there is a drop in the signal level between no paper and the presence of paper. This fact makes it very difficult, if not impossible, for this sensor to detect transparencies that do not have a white edge. It appears that transparencies could not be detected even if they were stopped under the sensor, i.e., no presence detection. U.S. Pat. No. 4,525,630 discloses an apparatus for detecting the presence of adhesive tape on a printed note, such as a banknote. The apparatus includes a means for illuminating a surface of this banknote, and detectors arranged to receive light reflected specularly and diffusely from an illuminated portion of the banknote. The presence of specularly reflective tape on the illuminated portion of the note is detected by measuring a ratio between specularly reflected light and diffusely reflected light. This ratio is indicative of the specularly reflective tape, since far more light is reflected specularly from the portion of the banknote repaired with tape than is reflected diffusely. In U.S. Pat. No. 4,754,148 an apparatus for evaluating a finish of a curved surface includes a light emitting means located at a predetermined angle to the curved surface, and a plurality of light receiving means for measuring intensity of light specularly reflected by the curved surfaces. Smoothness of the surface is determined by a means for calculating a ratio of the specular reflections.

Obviously, it would be desirable and of great benefit to provide a simple, cost effective sensor that can discriminate between both paper and transparencies without the need for ratio determining circuitry or adjustments.

Accordingly, a sensor is disclosed that can detect and discriminate between paper and transparency through the use of a light emitting diode and two detectors configured so as to measure both diffuse and specular reflectivity. The sensor also functions as a presence detector for either media.

For a better understanding of the present invention, reference may be had to the accompanying drawings wherein the same reference numerals have been applied to like parts and wherein.

Figure 1:
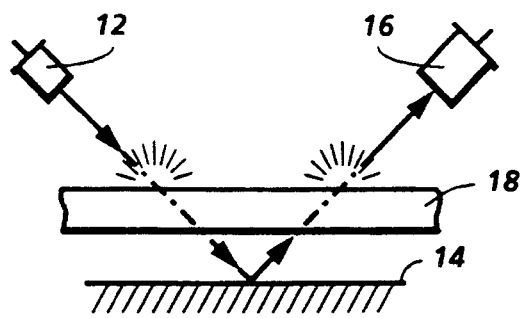
FIG. 1 is a prior art reflectance detector.

With reference to FIG. 1, there is shown a prior art reflectance detector sensor. Without paper in the paper path, a sufficient amount of light emitted from the light source 12 reflects from the mirror 14 to the detector 16 to indicate no paper. With paper 18 in the paper path, it is assumed that the light will be attenuated enough by the paper so that the amount of light reflected from mirror 14 to the reflectance detector 16 has diminished sufficiently to indicate the presence of paper in the path. Unfortunately, with highly translucent paper, not enough light will be attenuated by the paper such that the detector will not recognize the presence of the paper. Some of the light is diffused, but some is passed through the paper reflected off the mirror and goes back up through the paper again.

Figure 2:
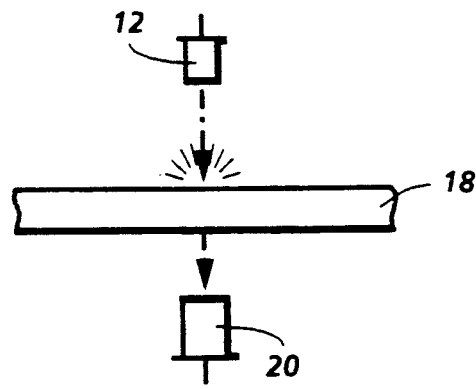
FIG. 2 is a prior art transmittance detector.

FIG. 2 shows another prior art sensor embodiment. In this case, the reflectance detector 16 has been replaced by transmittance detector 20.

Figure 3:
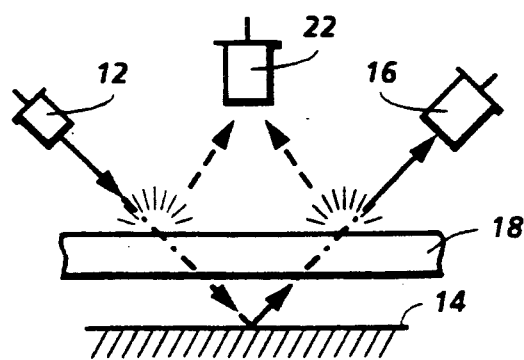
FIG. 3 is a prior art reflectance detector sensor.

As seen in FIG. 3, an additional detector 22 is added into the sensor of FIG. 1. This detector senses light that is diffusely reflected by the paper, that is, is not transmitted through the paper. Also, some of the light that is transmitted through the paper and reflected from the mirror 14 is diffused and scattered. So of this light also is sensed by the diffuse detector 22. It should be noted that the diffuse detector 22 is positioned to minimize detection by detector 22 of light reflected from mirror 14 with no paper present. Thus, if there is a narrow light beam from source 12 so that no light is reflected from mirror 14 to detector 22, then the position of detector 22, as shown, is suitable. The configuration will give a high contrast ratio and a great deal of latitude in selecting components.

If the light from source 12 is not narrow, it may be necessary to move the detector 22 out of the range of the reflected beam. If the detector is not moved, there will be a reduced output signal from the sensor. Therefore, there would be a decreased signal to noise ratio and a decreased maximum achievable contrast ratio.

Figure 4:
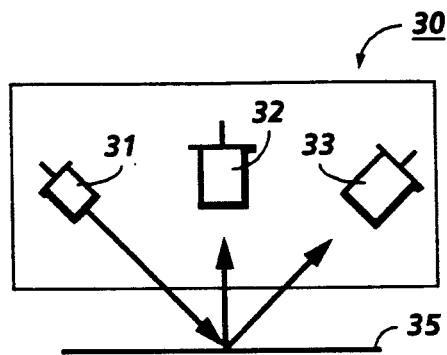
FIG. 4 is a sensor according to the present invention.
Figure 8:
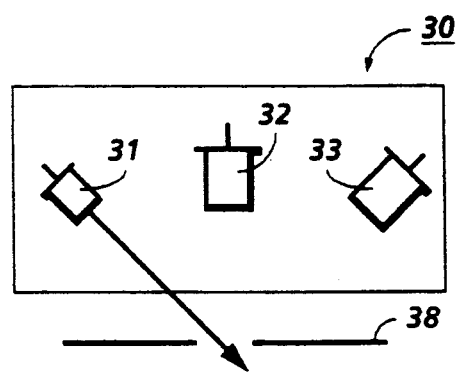
FIG. 8 shows a configuration of the present invention that incorporates a non-reflecting sheet support surface.
Figure 9:
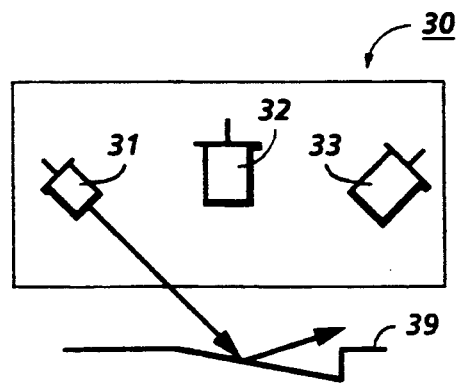
FIG. 9 shows an alternative sheet support surface to that of FIG. 8 in the form of a light redirecting surface.

In contrast to the heretofore mentioned prior art, the sensor 30 of the present invention can detect and discriminate between paper and transparency as well as act as a presence detector for either media. It comprises a three device package as shown in FIG. 4, that includes a suitable light source 31 (any suitable light emitter such as a light emitting diode) (LED) and two detectors 32 and 33 positioned above the media surface 35. The LED and detector 33 are at equal and opposite angles to the media while the second detector 32 is normal to the media surface. A non-reflective surface should be used for the target during the media absent condition. This can be accomplished with a low reflectance surface 38 as shown in FIG. 8 or with a redirecting surface 39 as shown in FIG. 9 that will direct the light beam from LED 31 away from the two detectors 32 and 33.

An example of an output logic for sensor 30 is as follows: (when connected as an emitter follower)

|  | Normal Detector | Angle Detector |
|---|---|---|
| paper present | high | low |
| transparency | don't care | high |
| trans on paper | high | high |
| no media | low | low |

As shown by the above chart, sensor 30 operates by responding to the diffuse reflectivity of paper by way of detector 32 that is normal to media and to specular reflectivity of a transparency with the angled detector 33. The two detectors 32 and 33 are set to thresholds that will correspond to the correct response for either paper or transparency. Thresholding is accomplished by using combinations of conventional focused detectors and light emitters, apertures, circuit gains, and logic output, i.e., conventional biased detectors or Schmitt trigger output. Preferably, lensed devices are used in order to obtain focused beams as opposed to fiber optics, since lensing will produce wanted collimation of the light. This also allows for greater sensor to media distance, which is often required in paper handling systems. An advantage of this sensor is that a ratio detection electronic scheme is not necessary. Preferably, sensor 30 uses level detection with biased Darlington detectors which will provide a simulated comparison signal, i.e., very high gain after a biased threshold level is reached.

Figure 5:
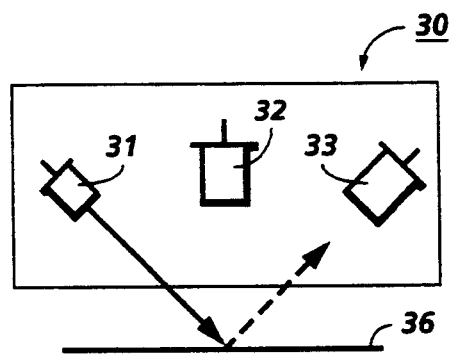
FIG. 5 is the sensor of the present invention shown sensing transparency.
Figure 6:
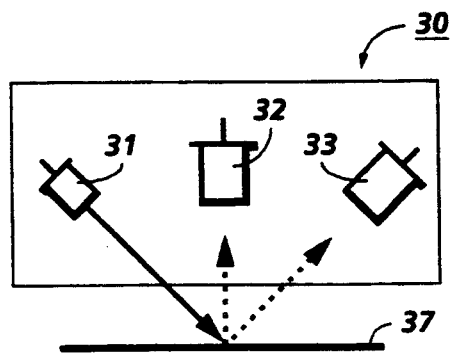
FIG. 6 is the sensor of the present invention shown sensing paper.
Figure 7:
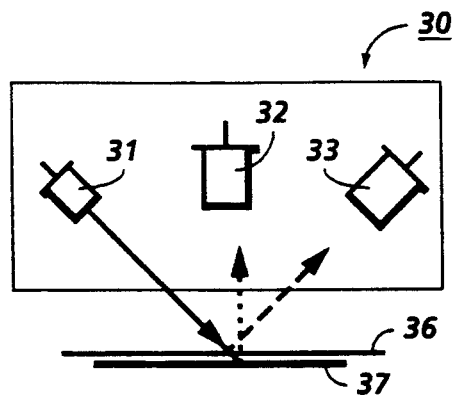
FIG. 7 is the sensor of the present invention sensing transparency on paper.

As shown in FIG. 5, when a transparency 36 passes sensor 30 the signal from normal detector 32 is low while the signal from angled detector 33 is high. When paper 37 passes underneath sensor 30 as shown in FIG. 6, the normal detector signal is high and the signal from the angled detector is low. With transparency on paper (such as paper backed transparency) as shown in FIG. 7, the angled detector will still produce a high output indicating a transparency is present. The normal detector may be high for this condition, however, this is a don't care logic state for this case. Naturally, if no media is beneath the sensor both detectors will give off low signals because of the use of non-reflecting or redirecting media support surfaces shown in FIGS. 8 and 9, respectively. Pre-calibration of sensor 30 is not required. The sensor can use visible or infrared light and views one spot on the media as opposed to full width viewing as required in some prior art sensors.

While there has been illustrated and described what is at present considered to be a preferred embodiment of the present invention, it will be appreciated that numerous changes and modifications are likely to occur to those skilled in the art, and it is intended in the appended claims to cover all those changes and modifications which fall within the true spirit and scope of the present invention.

We claim:

1. An apparatus adapted to detect and discriminate between paper and a transparency in a media path, comprising:
    an infrared lensed light source disposed near the media path for emitting light in the direction of the media path;
    a first lensed detector disposed adjacent to said light source; and
    a second lensed detector disposed adjacent to said first detector, said first and second detectors being configured to detect diffuse and specular reflectivity respectively of light reflected from a surface illuminated thereon by said light source, and wherein said light source and said second detector are positioned at an opposite angle with respect to the media path, and said first detector is positioned normal to the media path, and wherein said first detector has an opposite output signal than said second detector when viewing paper.

2. The apparatus of claim 1, wherein said light source is a light emitting diode.

3. The apparatus of claim 1, wherein a signal from said second detector when viewing a transparency traveling within the media path is opposite of that when viewing paper.

4. The apparatus of claim 3, wherein a signal from said second detector is the same relative level when viewing transparency on paper traveling within the media path.

5. The apparatus of claim 4, wherein when no media is present within the media path the signal from said first detector is opposite of that when paper was being viewed and the signal from said second detector is opposite of that when transparency was being viewed.

6. A sensing system for sensing whether paper, transparency or neither media is traveling within a media path, comprising:
- a media support surface as part of the media path, and wherein said media support surface includes an aperture therein adapted to receive light from a light source when no media is present on said media support surface in order to thereby render said media support surface non-reflecting;
- a lensed light emitting diode light source means positioned to project light toward the media path;
- first lensed detector means disposed adjacent said light source means for detecting light therefrom; and
- second detector means disposed adjacent with said first detector means and said light source means for detecting light emitted from said light source means, and wherein said first and second detectors are configured to respectively sense diffuse and specular reflectivity of light reflected from a surface illuminated by said light source means.

7. A sensing system for sensing whether paper, transparency or neither media is traveling within a media path, comprising:
- a light redirecting media support surface as part of the media path;
- a lensed light emitting diode light source means positioned to project light toward the media path;
- first lensed detector means disposed adjacent said light source means for detecting light therefrom; and
- second detector means disposed adjacent with said first detector means and said light source means for detecting light emitted from said light source means, and wherein said first and second detectors are configured to respectively sense diffuse and specular reflectivity of light reflected from a surface illuminated by said light source means, and wherein said media support surface includes portions thereof positioned and configured in multiple planes with respect to a horizontal plane in order to deflect light from a light source away from said first and second detectors.

8. A sensing system for sensing whether paper, transparency or neither media is traveling within a media path, comprising:
- a non-reflective media support surface;
- a lensed light source means positioned to project light toward the media path;
- first lensed detector means disposed adjacent said light source means for detecting light therefrom; and
- second detector means disposed adjacent with said first detector means and said light source means for detecting light emitted from said light source means, and wherein said light source and said second detector are positioned at opposite angles with respect to the media, and said first detector is positioned normal to the media path, and wherein said first detector has an opposite output signal than said second detector when viewing paper.

9. The apparatus of claim 8, wherein a signal from said second detector when viewing a transparency traveling within the media path is opposite of that when viewing paper.

10. The apparatus of claim 9, wherein a signal from said second detector is the same relative level when viewing transparency on paper traveling within the media path.

11. The apparatus of claim 10, wherein when no media is present within the paper path the signal from said first detector is opposite of that when paper was being viewed and the signal from said second detector is opposite of that when transparency was being viewed.

* * * * *